United States Patent
Planas et al.

(10) Patent No.: US 11,819,805 B2
(45) Date of Patent: Nov. 21, 2023

(54) SYSTEM AND METHOD OF DYNAMICALLY ADJUSTING FLUID FLOW RATE IN RESPONSE TO PRESSURE

(71) Applicant: Fenwal, Inc., Lake Zurich, IL (US)

(72) Inventors: Samantha Michalski Planas, Wauconda, IL (US); Hannah Meiselman, Baltimore, MD (US)

(73) Assignee: Fenwal, Inc., Lake Zurich, IL (US)

( * ) Notice: Subject to any disclaimer, the term of this patent is extended or adjusted under 35 U.S.C. 154(b) by 1101 days.

(21) Appl. No.: 16/509,556

(22) Filed: Jul. 12, 2019

(65) Prior Publication Data

US 2020/0016539 A1    Jan. 16, 2020

Related U.S. Application Data

(60) Provisional application No. 62/697,689, filed on Jul. 13, 2018.

(51) Int. Cl.
*B01D 61/22* (2006.01)
*A61M 1/36* (2006.01)
*A61M 1/02* (2006.01)

(52) U.S. Cl.
CPC .............. *B01D 61/22* (2013.01); *A61M 1/02* (2013.01); *A61M 1/3633* (2013.01); *B01D 2311/14* (2013.01)

(58) Field of Classification Search
None
See application file for complete search history.

(56) References Cited

U.S. PATENT DOCUMENTS

| | | | |
|---|---|---|---|
| 5,053,121 A | 10/1991 | Schoendorfer et al. | |
| 5,194,145 A | 3/1993 | Schoendorfer | |
| 5,868,696 A | 2/1999 | Giesler et al. | |
| 5,954,971 A * | 9/1999 | Pages .................. | A61M 1/3646 210/90 |
| 6,419,822 B2 | 7/2002 | Muller et al. | |

(Continued)

FOREIGN PATENT DOCUMENTS

| | | |
|---|---|---|
| WO | WO 92/02264 A1 | 2/1992 |
| WO | WO 2008/056733 A1 | 5/2008 |
| WO | WO 2014/039086 A1 | 3/2014 |

OTHER PUBLICATIONS

Extended European Search Report for Application No. 19185910.7 dated Nov. 27, 2019.

*Primary Examiner* — Hayden Brewster
(74) *Attorney, Agent, or Firm* — Cook Alex Ltd.

(57) ABSTRACT

The pressure of fluid being conveyed through a fluid flow path during a biological fluid procedure is detected during the procedure. The fluid is conveyed through the fluid flow path 1) at a first pre-determined rate if pressure is zero to a first pressure threshold; 2) at the first pre-determined rate if pressure is greater than the first pressure threshold but less than or equal to a second pressure threshold and if an immediately preceding rate is equal to the first pre-determined rate; 3) at a second pre-determined rate if pressure is greater than the first pressure threshold but less than or equal to the second pressure threshold and if an immediately preceding rate is equal to the second pre-determined rate; and 4) at the second pre-determined rate if pressure value is greater than the second pressure threshold but less than or equal to a third pressure threshold.

20 Claims, 7 Drawing Sheets

(56) References Cited

U.S. PATENT DOCUMENTS

| | | |
|---|---|---|
| 8,840,790 B2 | 9/2014 | Wegener et al. |
| 2009/0211962 A1 | 8/2009 | Min et al. |
| 2012/0273416 A1 | 11/2012 | Wegener et al. |
| 2016/0378298 A1 | 12/2016 | Planas et al. |
| 2018/0055986 A1 | 3/2018 | Brown et al. |
| 2019/0060547 A1 | 2/2019 | Kusters |

* cited by examiner

SYSTEM AND METHOD OF DYNAMICALLY ADJUSTING FLUID FLOW RATE IN RESPONSE TO PRESSURE

CROSS-REFERENCE TO RELATED APPLICATIONS

This application claims the benefit of and priority of U.S. Provisional Patent Application Ser. No. 62/697,689, filed Jul. 13, 2018, the contents of which are incorporated by reference herein.

FIELD OF THE DISCLOSURE

The present disclosure relates generally to systems and methods of dynamically adjusting fluid pump rate in response to and in order to adjust pressure and, in particular to systems and methods for adjusting flow rates of blood components in response to pressure sensed by a pressure sensor at a blood component filter.

BACKGROUND

The separation of blood into its components is commonly performed in apheresis procedures, in which blood components are separated while a donor or patient is connected to a separation system (sometimes referred to as a "chairside" procedure), or with previously-collected whole blood, in whole blood manufacturing or component processing procedures. For example, a common procedure is the separation of whole blood into plasma and red blood cells.

Such separation procedures may be highly automated, utilizing a single-use fluid circuit comprising containers of various solutions, such as saline, anticoagulant and additive solution, as well as cassettes comprising defined fluid pathways, as well as containers for the receipt of the separated blood components, all of which may be interconnected by fluid flow paths in the form of tubing to a separation device, such as a centrifuge or a spinning membrane separator. The fluid circuit is associated with a durable hardware component which has pumps and clamps associated therewith that operatively engage the tubings to circulate the blood and its separated components through the associated single-use fluid circuit. The durable hardware component may include a programmable controller to automatically operate the pumps, clamps and separator in accordance with the desired apheresis procedure.

Before transfusing collected blood components to a recipient in need of a component, or before subjecting blood components to treatment, it may be desirable to minimize the presence of impurities or other materials that may cause undesired side effects in the recipient. For example, because of possible reactions, it may be desirable to reduce the number of leukocytes in blood components before storage, or at least before transfusion (i.e., "leukoreduction"). Such leukoreduction may be accomplished by flowing the blood components through a leukoreduction filter (also called a leukofilter) that captures white blood cells by requiring passage of the component through a filter medium that retains the undesired leukocytes and other components/aggregates while allowing the remaining desirable components to pass through the medium and be collected for subsequent transfusion and/or storage. In the case of disposable leukofilters, the used filters may thereafter be discarded.

SUMMARY

According to an aspect of the present disclosure, a system is provided for monitoring and controlling fluid pressure during a biological fluid procedure comprising a plurality of procedure phases. The system comprises a reusable separation apparatus controlled by a controller, with the reusable separation apparatus comprising a pressure sensor and a pump having an adjustable flow rate in communication with the controller. A sterile circuit is configured to associate with the reusable separation apparatus and provide a fluid flow path in association with the pressure sensor. The pump is configured to pump fluid through the fluid flow path, while the controller is configured to control operation of the pump. In particular, the controller controls the pump to pump fluid through the fluid flow path at a first pre-determined pump rate when the pressure sensor detects a first measured pressure value in the range of zero to a first pre-determined pressure threshold. Fluid is pumped through the fluid flow path at the first pre-determined pump rate when the pressure sensor detects a second measured pressure value greater than the first pre-determined pressure threshold but less than or equal to a second pre-determined pressure threshold and when an immediately preceding pump rate is equal to the first pre-determined pump rate. Fluid is pumped through the fluid flow path at a second pre-determined pump rate when the pressure sensor detects a third measured pressure value greater than the first pre-determined pressure threshold but less than or equal to the second pre-determined pressure threshold and when an immediately preceding pump rate is equal to the second pre-determined pump rate. Fluid is pumped through the fluid flow path at the second pre-determined pump rate when the pressure sensor detects a fourth measured pressure value greater than the second pre-determined pressure threshold but less than or equal to a third pre-determined pressure threshold.

According to another aspect of the present disclosure, a method is provided for monitoring and controlling fluid pressure during a biological fluid procedure comprising a plurality of procedure phases. Fluid is conveyed through the fluid flow path at a first pre-determined rate when a first measured pressure value in the range of zero to a first pre-determined pressure threshold is detected. Fluid is conveyed through the fluid flow path at the first pre-determined rate when a second measured pressure value greater than the first pre-determined pressure threshold but less than or equal to a second pre-determined pressure threshold is detected and when an immediately preceding rate is equal to the first pre-determined rate. Fluid is conveyed through the fluid flow path at a second pre-determined rate when a third measured pressure value greater than the first pre-determined pressure threshold but less than or equal to the second pre-determined pressure threshold is detected and when an immediately preceding rate is equal to the second pre-determined rate. Fluid is pumped through the fluid flow path at the second pre-determined rate when a fourth measured pressure value greater than the second pre-determined pressure threshold but less than or equal to a third pre-determined pressure threshold is detected.

According to yet another aspect of the present disclosure, a method is provided for monitoring and controlling fluid pressure during a biological fluid procedure comprising a plurality of procedure phases. Fluid is conveyed through the fluid flow path at a first pre-determined rate when a first measured pressure value in the range of zero to a first pre-determined pressure threshold is detected. Fluid is conveyed through the fluid flow path at the first pre-determined rate when a second measured pressure value greater than the first pre-determined pressure threshold but less than or equal to a second pre-determined pressure threshold is detected and when an immediately preceding rate is equal to the first pre-determined rate. Fluid is conveyed through the fluid flow path at a second pre-determined rate when a third measured pressure value greater than the first pre-determined pressure threshold but less than or equal to the second pre-determined pressure threshold is detected and when an immediately preceding rate is equal to the second pre-determined rate. Fluid is conveyed through the fluid flow path at the second pre-determined rate when a fourth measured pressure value greater than the second pre-determined pressure threshold but less than or equal to a third pre-determined pressure threshold is detected. Fluid is conveyed through the fluid flow path at the second pre-determined rate when a fifth measured pressure value greater than the third pre-determined pressure threshold but less than or equal to a fourth pre-determined pressure threshold is detected and when an immediately preceding rate is equal to the second pre-determined rate. Fluid is conveyed through the fluid flow path at a third pre-determined rate comprising a rate from a previous phase when a sixth measured pressure value greater than the third pre-determined pressure threshold but less than or equal to the fourth pre-determined pressure threshold is detected and when an immediately preceding rate is equal to the third pre-determined rate. Fluid is conveyed through the fluid flow path at the third pre-determined rate when a seventh measured pressure value greater than the fourth pre-determined pressure threshold but less than or equal to a fifth pre-determined pressure threshold is detected. Fluid is conveyed through the fluid flow path at the third pre-determined rate when an eighth measured pressure value greater than the fifth pre-determined pressure threshold but less than or equal to a sixth pre-determined pressure threshold is detected and when an immediately preceding rate is equal to the third pre-determined rate. Fluid is conveyed through the fluid flow path at a fourth pre-determined rate when a ninth measured pressure value greater than the fifth pre-determined pressure threshold but less than or equal to the sixth pre-determined pressure threshold is detected and when an immediately preceding rate is equal to the fourth pre-determined rate. Fluid is conveyed through the fluid flow path at the fourth pre-determined rate when a tenth measured pressure value greater than the sixth pre-determined pressure threshold is detected.

BRIEF DESCRIPTION OF THE DRAWINGS

Features, aspects, and advantages of the present embodiments will become apparent from the following description, appended claims, and the accompanying exemplary embodiments shown in the drawings, which are briefly described below.

DETAILED DESCRIPTION

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

Some embodiments may utilize leukoreduction filter inlet pressure measurements to manage fluid flow rates in order to maintain low filter pressures, while achieving short procedure times while washing/recovering retentate with additive solution/wash solution.

When washing residual cells from a fluid circuit of a fluid processing procedure, some embodiments may allow for variable and dynamic wash rates based on varying filter pressure.

Some embodiments may allow for fluid flow rates during cell washing to increase when filter pressures reach lower levels, even when filter pressure had previously reached higher levels warranting a recent flow rate decrease.

Some embodiments may allow for more gradual pressure gradients in order to decrease procedure time and/or reduce time-averaged pressure.

There have been continuing efforts to automate the apparatus and systems used in the post-collection processing of whole blood, and an automated blood component separator for such post-collection processing may be employed. One class of such automated separators employs relatively rotating surfaces, at least one of which carries a porous membrane. An example of such a membrane separator is disclosed in PCT Patent Application Publication No. WO 2014/039086 A1, which is incorporated by reference in its entirety, although any suitable membrane separator may be used. Another class employs a centrifuge that utilizes centrifugal separation principles. An exemplary centrifugal separator is disclosed in U.S. Pat. No. 5,868,696, which is incorporated by reference in its entirety, although any suitable centrifugal separator may be used.

Both membrane separation and centrifugal separation systems may involve a durable processing system or device used in combination with a disposable processing set or circuit. The durable processing system may include a pump assembly that interacts with one or more of the components of the disposable circuit to draw blood or other bodily fluid from a blood source and move the blood or bodily fluid to another location within the disposable circuit by moving fluid through a fluid flow path.

Figure 1:
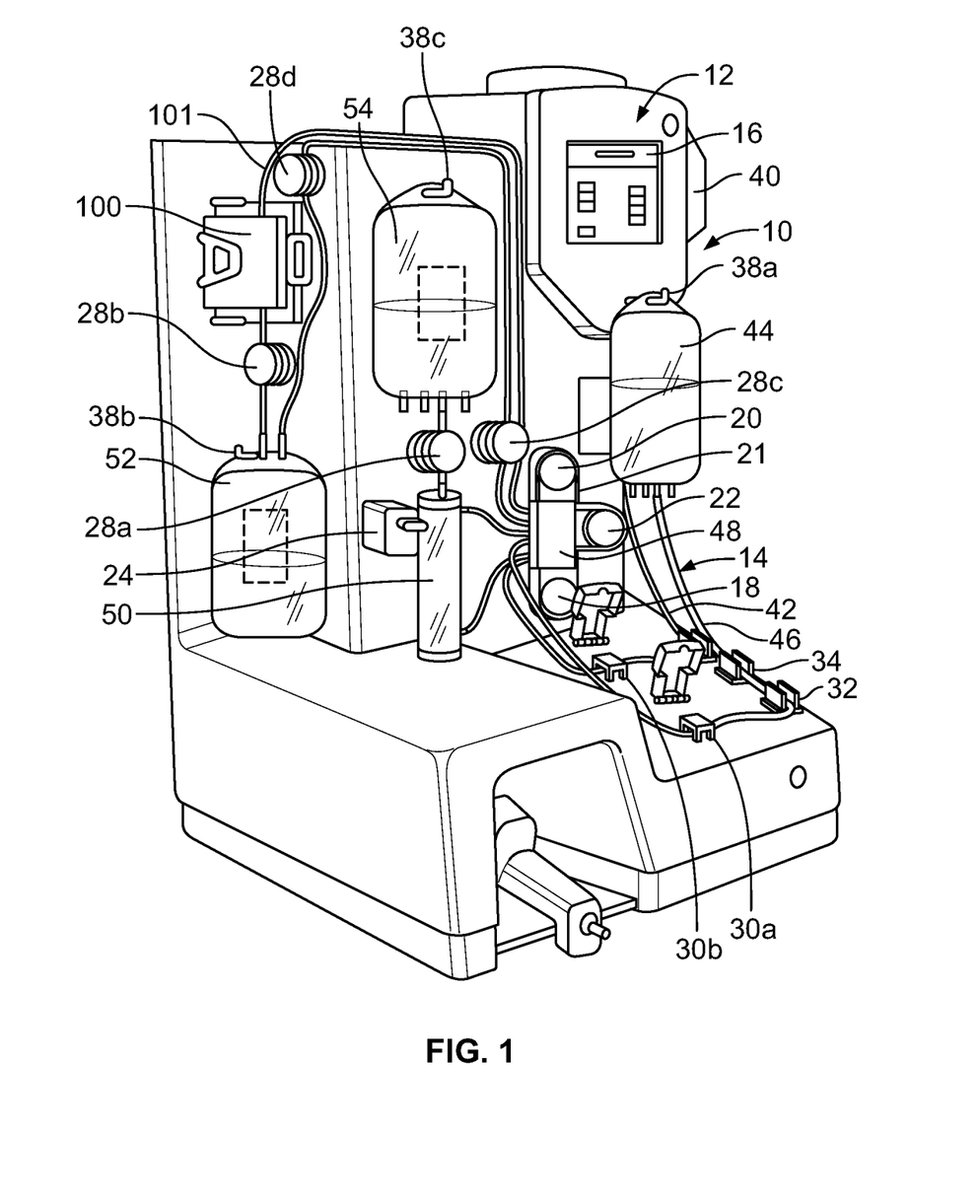
FIG. 1 is a blood processing system, which includes a durable reusable processing device and a disposable fluid flow circuit, according to an exemplary embodiment.

FIG. 1 depicts a blood processing system, generally at 10, which includes a durable reusable processing device 12 and a disposable fluid flow circuit 14 for processing collected whole blood. The illustrated blood processing device 12 includes associated pumps, valves, sensors, displays and other apparatus for configuring and controlling flow of blood and additive solution through the disposable circuit. The device and the processing may be directed by an internal controller that includes a programmable microprocessor automatically controlling the operation of the pumps, valves, sensors, etc.

The processing device 12 may include a user input and output touch screen 16, a pump station including a source fluid pump 18, e.g, whole blood pump, a retentate pump 20, e.g., an RBC pump, an additive solution pump 22, blood separator mounting station and drive unit 24, tubing clamps 28a-28d, sterile connection or docking devices 30a, 30b, one or more tubing clamps 32, and hematocrit sensor 34. The processing device may also include hangers 38a-c, each associated with a weight scale, for suspending the various containers of the disposable fluid circuit 14.

The fluid flow circuit 14 may include an additive solution container 40 and associated fluid flow tubing 42 for withdrawing the additive solution, a source container 44, e.g., a whole blood container, and associated fluid flow tubing 46 for withdrawal of, e.g., collected whole blood from the container, and a processing module that includes pump cassette 48, separator 50 (e.g., spinning membrane separator, separation chamber placed within a centrifuge), retentate container 52 (e.g., configured to receive separated red blood cells), filtrate container 54 (e.g., configured to receive separated plasma), and associated connecting tubing. The pump cassette 48 may route the fluid flow through tubing loops 21 that extend from the cassette 48, and each loop 21 may be uniquely positioned to engage a particular one of the pumps 18, 20, and 22. The tubing may extend through the cassette 48 or the cassette 48 may have pre-formed fluid flow paths that direct the fluid flow.

For reducing the number of leukocytes that may be present in the separated red blood cells, the fluid flow circuit 14 may include a leukocyte reduction filter or leukoreduction filter 100 (or leukofilter), which may be of any suitable construction for removing leukocytes from concentrated red blood cells without unduly causing hemolysis of red blood cells or reducing the number of red blood cells in the collected product. In one embodiment, the leukofilter 100 may communicate with a pressure sensor 102 (FIG. 2) for monitoring the pressure, e.g., along tubing 101 leading into the leukofilter 100. An example of a leukocyte reduction filter may be found in U.S. Patent Publication No. 2018/0055986 A1, which is incorporated herein by reference in its entirety, although any suitable leukofilter may be used.

Figure 2:
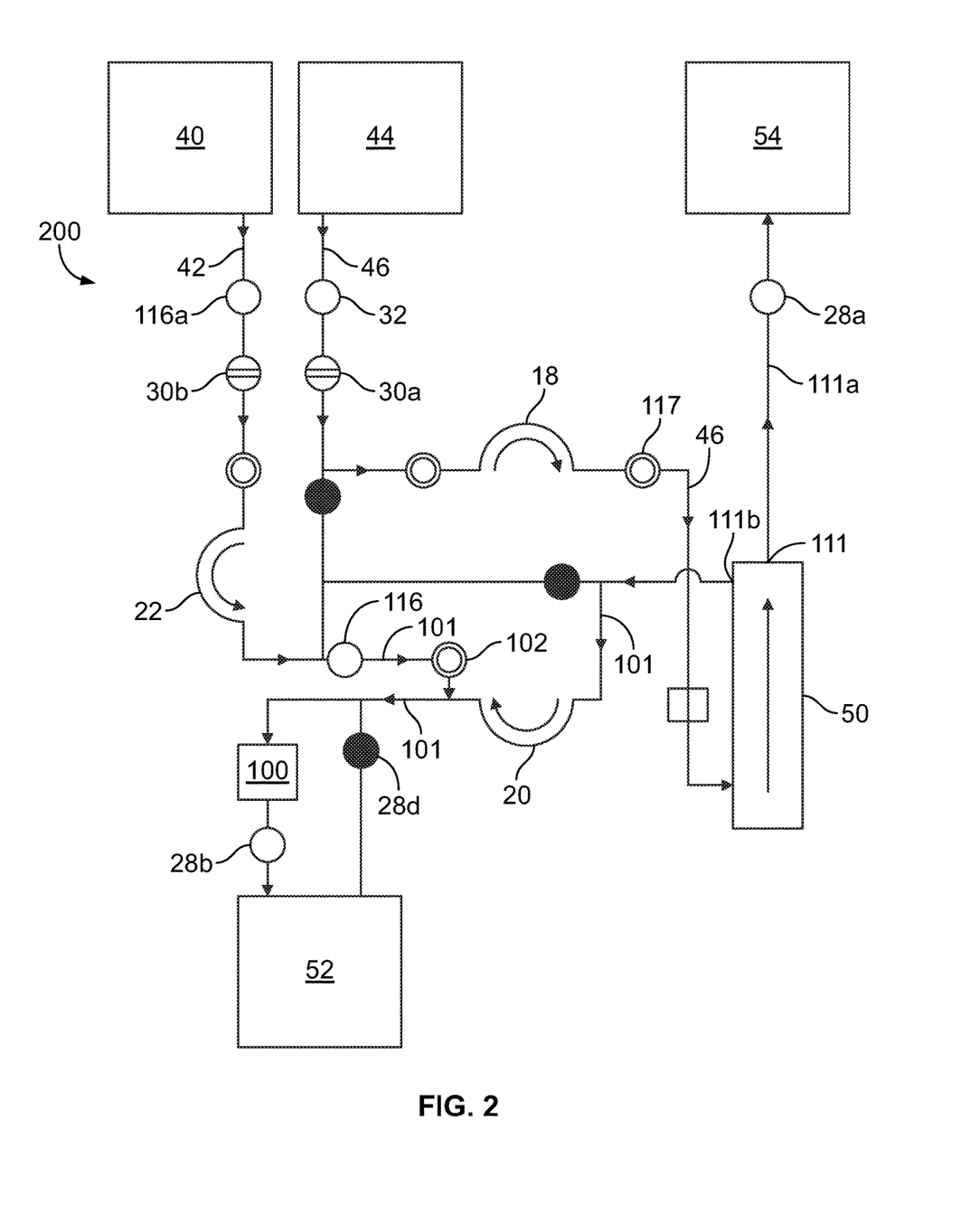
FIG. 2 is schematic diagram of a blood processing system during separation of source fluid, according to an exemplary embodiment.

Turning now to FIG. 2, components of the disposable fluid flow circuit 14 and the durable reusable processing device 12 of FIG. 1 during separation of source fluid are schematically illustrated. System 200, illustrated in FIG. 2, includes the source container 44, which may be any suitable container but in one embodiment may be a flexible plastic pouch or bag in which a volume of source fluid, e.g., blood component(s), have been previously collected. In the case in which the source fluid is whole blood, approximately 450-600 ml (a typical "unit") of whole blood may have been previously collected. The container 44 may be part of a separate system during collection and then joined to the rest of the fluid circuit 14 (FIG. 1) or connected to the remainder of the circuit 14 at the time of collection. In the case in which source container 44 contains whole blood, at the time of collection, in accordance with customary procedure, the whole blood may be mixed with an anticoagulant to prevent premature coagulation. Accordingly, "whole blood" as used herein includes blood mixed with anticoagulant.

Flexible plastic tubing 46 may be attached to the source container 44, such as by a sterile connection device or other suitable attachment mechanism, and defines a source fluid flow path between the source container 44 and an inlet port in the separator 50. The source fluid separates within the separator 50 into retentate and filtrate. Filtrate fluid may exit through filtrate outlet 111 of the separator 50 into the filtrate container 54. Retentate fluid may exit through retentate outlet 111b through tubing 101. In one embodiment, the retentate may be concentrated red blood cells. In one embodiment, the filtrate may be plasma.

In an embodiment in which retentate comprises red blood cells, the system 200 may include a leukocyte reduction filter 100 to remove leukocytes that may be present in the red blood cells. The retentate may flow along tubing 101 from the separator 50 through the leukocyte reduction filter 100 into storage container 52, which may be of any suitable plastic material compatible with cell storage.

For controlling flow of source fluid into the separator 50, the system 200 may include an inlet pump 18, which may be of any suitable construction, and may be, for example, a peristaltic type pump which operates by progressive compression or squeezing of the tubing 46 forming the inlet flow path into the separator 50, a flexible diaphragm pump, or other suitable pump. A pressure sensor 117 may communicate with the inlet flow path between the pump 18 and the separator 50 to determine the pressure near or within the separator 50.

To control the flow rate of retentate from the separator 50, the system 200 may also include an outlet pump 20 that is associated with the outlet flow path 101, and may function in the manner similar to that described with respect to inlet pump 18. Outlet pump 20 also may be of any suitable construction such as a peristaltic pump, a flexible diaphragm, or other suitable pumping structure. In one embodiment, the filtrate flow path 111a exiting the separator 50 is not controlled by a pump, and the volumetric flow rate through the filtrate flow path tubing 111a is the difference between the inlet volumetric flow rate from inlet pump 18 and the outlet volumetric flow rate from outlet pump 20. The system 200 may, however, include a clamp 28a for controlling flow of filtrate through the filtrate flow path tubing 111a.

The system 200 may also include an inlet clamp or valve or solenoid 116a which may be operated to control fluid from a cell preservative/wash container 40. Flexible plastic tubing 42 may be attached to the wash solution container 40, such as by a sterile connection device or other suitable attachment mechanism. Tubing 42 may define a fluid flow path between the wash solution container 42 and a valve or clamp 116, where wash solution flow may be directed to inlet flow path 46 and/or outlet flow path 101. To control the flow rate of wash solution from the wash solution container 40, the system 200 may include a wash solution pump 22 that is associated with flow path 42 directing wash solution into inlet flow path 46 and/or outlet flow path 101. Pump 22 may function in the manner similar to that described with respect to inlet pump 18 and outlet pump 20.

The fluid circuit 14 (FIG. 1) may include a filtrate collection container 54 in fluid communication with the filtrate flow path 111a for receiving filtrate separated by the separator 50. In an embodiment in which the filtrate is plasma, because the plasma passes through a porous membrane in the separator 50, the plasma that is collected in container 54 may be largely cell free plasma and may be suitable for administration to patients, freezing for storage, and/or subsequent processing.

The durable controller may comprise a microprocessing unit driven by software, with certain steps performed by a human operator/user. For example, the controller, when switched on, may conduct self-calibration checks, including the checking of the pumps, clamps, and sensors. The controller may then prompt the user to enter selected procedural parameters, such as the fluid procedure to be performed, the amount of fluid to be processed, the number of procedures to take place, etc. The operator may then select and enter the procedural parameters for the fluid procedure.

Turning to FIG. 2, fluid flow during a separation phase of the source fluid will be described, according to an exemplary embodiment. During separation, source fluid may be withdrawn from a source fluid container 44 via inlet flow path 46 towards the separator 50. Flow rate of the source fluid into the separator 50 may be controlled by the inlet pump 18, which in one embodiment, may pump fluid into the separator 50 at a flow rate in the range of 40-60 mL/min, although the flow rate used may be any suitable flow rate based on the constituents to be separated, filtration rate of the separator, etc. Source fluid may be separated within the separator 50, and retentate may be pumped out of the retentate outlet 111b of the separator 50 via an outlet pump 20 pumping retentate along outlet flow path 101 through leukofilter 100 into the retentate container 52. In one embodiment, the outlet pump 20 may pump retentate out of the separator 50 at a flow rate in the range of 15-20 mL/min. In parallel with the outlet pump 20, the wash solution pump 22 may pump wash solution from container 40 via flow path 42 towards the retentate outlet flow path 101. A leukofilter pressure sensor 102 in communication with outlet flow paths of pumps 20 and 22 may detect a pressure corresponding to an additive flow rate of 17-24 mL/min, which is the sum of the flow rates of pumps 20 and 22. Flow rate of the filtrate exiting through filtrate outlet 111 into filtrate container 54 along filtrate flow path 111a may be determined by the difference between the inlet flow rate of 40-60 mL/min and the outlet flow rate of 15-20 mL/min, resulting in a filtrate outlet flow rate of 20-45 mL/min. The separation phase may take place until the source fluid container 44 is empty or until a desired amount of source fluid has been processed.

Figure 6:
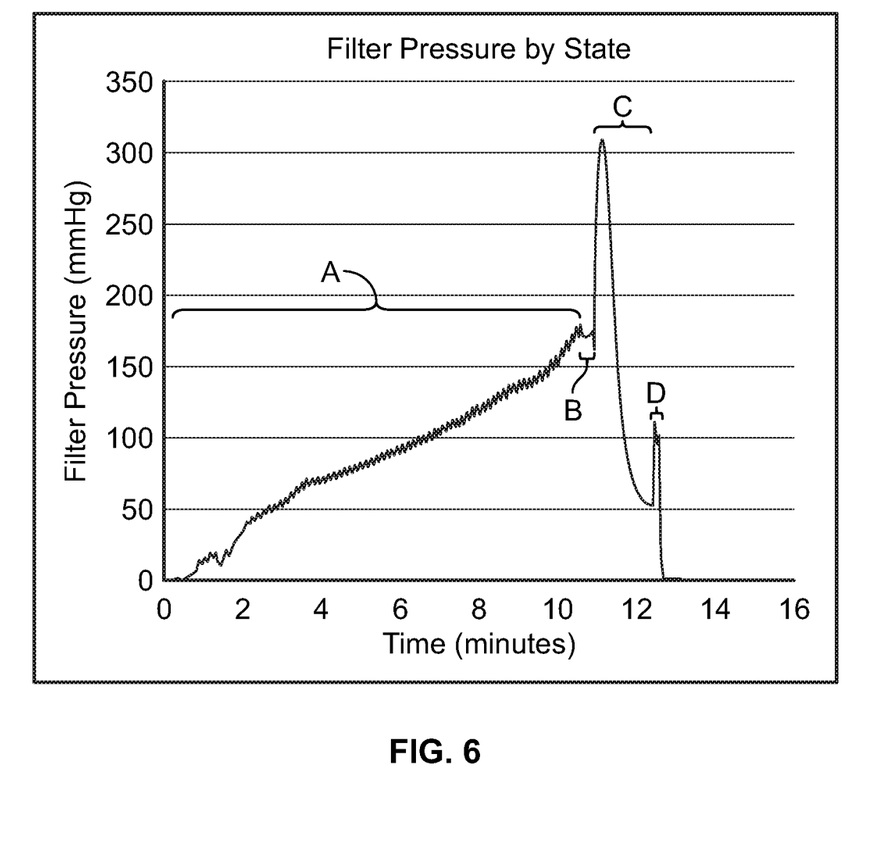
FIG. 6 is a graph of pressure sensed by a pressure sensor plotter over time during a fluid processing procedure, according to an exemplary embodiment.

FIG. 6 shows a graphical illustration of the pressure sensed by pressure sensor 102 over time during the fluid procedure, according to an exemplary embodiment. Segment A of FIG. 6 corresponds to the separation phase of a fluid procedure (e.g., as shown in FIG. 2) and depicts the leukofilter pressure increasing steadily over time during separation as increasing amounts of retentate, e.g., white blood cells, red blood cells, collect at the leukofilter 100. The embodiment of FIG. 6 shows filter pressure starting out at less than 100 mmHg and steadily increasing towards 200 mmHg.

Figure 3:
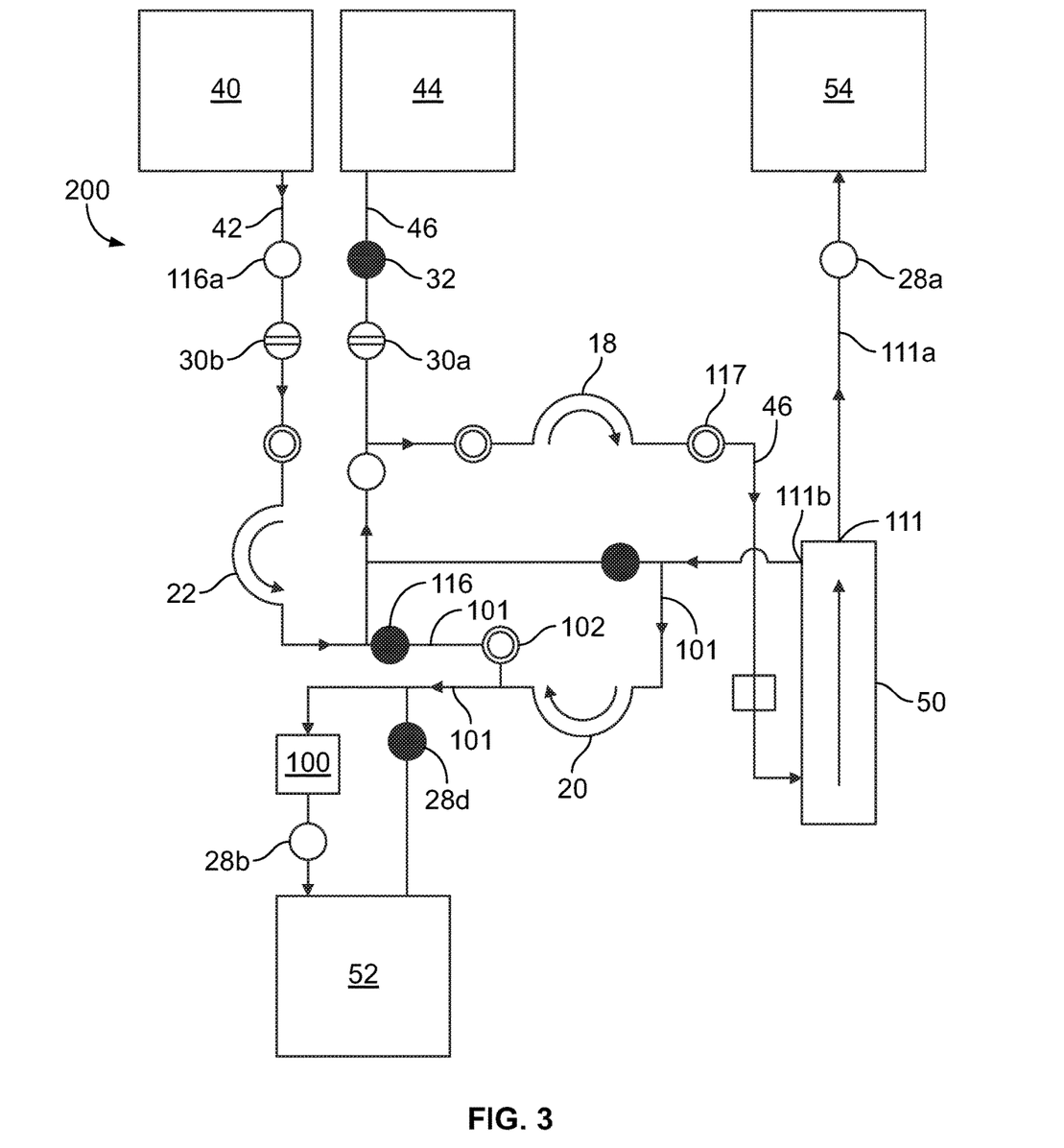
FIG. 3 is a schematic diagram of a blood processing system during a follow-through phase of the fluid procedure in which a desired amount of source fluid has been withdrawn but fluid from the remainder of the system may be collected with wash solution, according to an exemplary embodiment.

FIG. 3 is a schematic illustration of the components of the system 200 during a follow-through phase of the fluid procedure in which a desired amount of source fluid has been withdrawn from container 44 but further fluid from the separator 50 and the remainder of the system 200 may be collected with wash solution from container 40. During the follow-through phase, the source fluid clamp 32 may be closed so that no further source fluid may be withdrawn from container 44. Wash solution may be withdrawn from container 40 via flow path 42 towards the inlet flow path 46 and into the separator 50. The flow rate of the wash solution into the separator 50 may be controlled by wash solution pump 22 and/or inlet pump 18, which in one embodiment, may pump fluid into the separator 50 at a flow rate in the range of 40-60 mL/min. Valve 116 may be closed to direct the wash solution into inlet flow path 46 rather than into outlet flow path 101. Remaining source fluid within the separator 50 may be washed by the wash solution within the separator 50, and remaining retentate may be pumped out of the retentate outlet 111b of the separator 50 via the outlet pump 20 pumping retentate along outlet flow path 101 through leukofilter 100 into the retentate container 52. The outlet pump 20 may be configured to pump retentate out of the separator 50 at the same flow rate as the outlet pump rate of the most recent phase, i.e., the separation phase, which, in one embodiment, may be in the range of 15-20 mL/min. The outlet pump flow rate during the follow-through phase is hereinafter designated FollowMinFlushRate. The leukofilter pressure sensor 102 in communication only with the outlet flow path 101 of pump 20 in the follow-through phase may now detect a pressure corresponding only to the flow rate of outlet pump 20. The flow rate of the filtrate exiting through filtrate outlet 111 into filtrate container 54 along filtrate flow path 111a may be determined by the difference between the inlet flow rate of 40-60 mL/min and the outlet flow rate of 15-20 mL/min, resulting in a filtrate outlet flow rate of 20-45 mL/min.

Segment B of FIG. 6 corresponds to the follow-through phase of the fluid procedure (e.g., as shown in FIG. 3) and depicts the leukofilter pressure remaining similar to the end of the separation phase (segment A) as fluid from the separator continues to be pumped through the leukofilter 100. In some embodiments, the pressure may increase during segment B (e.g., due to cessation of wash solution mixing with retentate leaving the separator 50) or decrease (e.g., due to reduced flow rate of retentate and/or the dilution of retentate by the follow-through of high-viscosity retentate, e.g., high hematocrit blood, with a low-viscosity solution).

Figure 4:
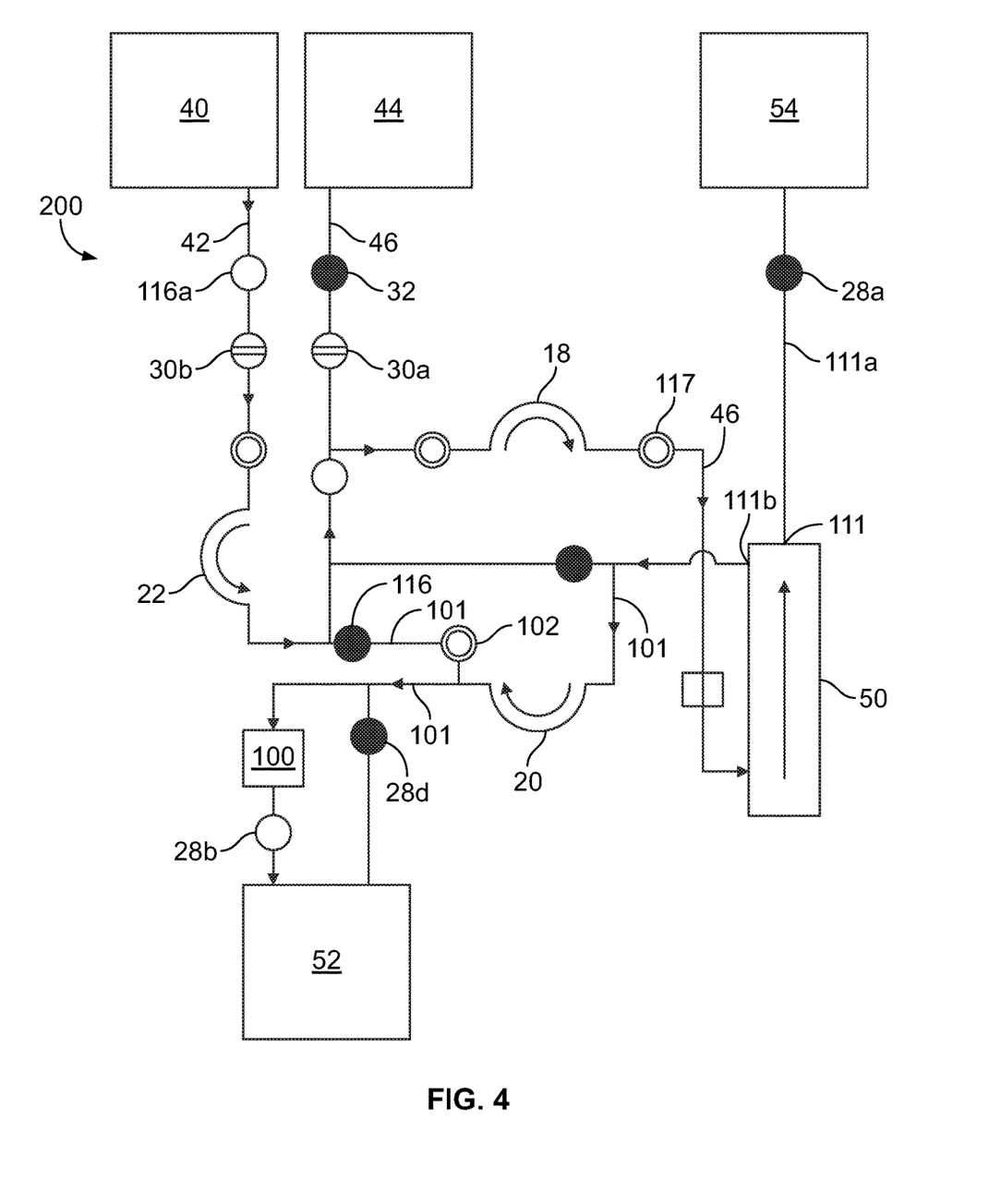
FIG. 4 is a schematic diagram of a blood processing system during a fluid flush phase of the fluid procedure in which retentate may be collected with wash solution, according to an exemplary embodiment.

FIG. 4 is a schematic illustration of the components of the system 200 during a fluid flush phase of the fluid procedure in which retentate from the separator 50 may be collected with wash solution from container 40. The fluid flush phase may also serve to recover retentate from the leukofilter 100, bring the retentate product to a final desired volume, and/or add additive solution to prepare the product for storage. During the fluid flush phase, the source fluid clamp 32 may again be closed so that no further source fluid may be withdrawn from container 44. The filtrate flow clamp 28a may also be closed so that all fluid pumped into the separator may exit through retentate outlet 111b. Wash solution may be withdrawn from container 40 via flow path 42 towards the inlet flow path 46 and into the separator 50. The flow rate of the wash solution into the separator 50 may be controlled by wash solution pump 22 and/or inlet pump 18, which may pump fluid into the separator 50 at a flow rate determined by a programmable algorithm based on the pressures sensed by leukofilter pressure sensor 102 that will be described further below. Valve 116 may be closed to direct the wash solution into inlet flow path 46 rather than into outlet flow path 101. Remaining fluid may be pumped out of the retentate outlet 111b of the separator 50 via the outlet pump 20 pumping retentate along outlet flow path 101 through leukofilter 100 into the retentate container 52. The outlet pump 20 may be configured to pump retentate out of the separator 50 at a flow rate determined by a programmable algorithm incorporating pressure readings from, e.g., the sensor 102. The outlet pump flow rate may be configured to be the same flow rate as the pump rates of pumps 22 and/or 18. Similarly to the follow-through phase, the leukofilter pressure sensor 102 in communication only with the outlet flow path 101 of outlet pump 20 in the fluid flush phase may now detect a pressure corresponding only to the flow rate of outlet pump 20.

Segment C of FIG. 6 corresponds to the fluid flush phase of the fluid procedure (e.g., as shown in FIG. 4) and depicts the leukofilter pressure spiking quickly approximately from its previous pressure to more than 300 mmHg when fluid from the separator 50 is again pumped through the leukofilter 100 during the fluid flush phase and then falling to approximately 50 mmHg.

Figure 5:
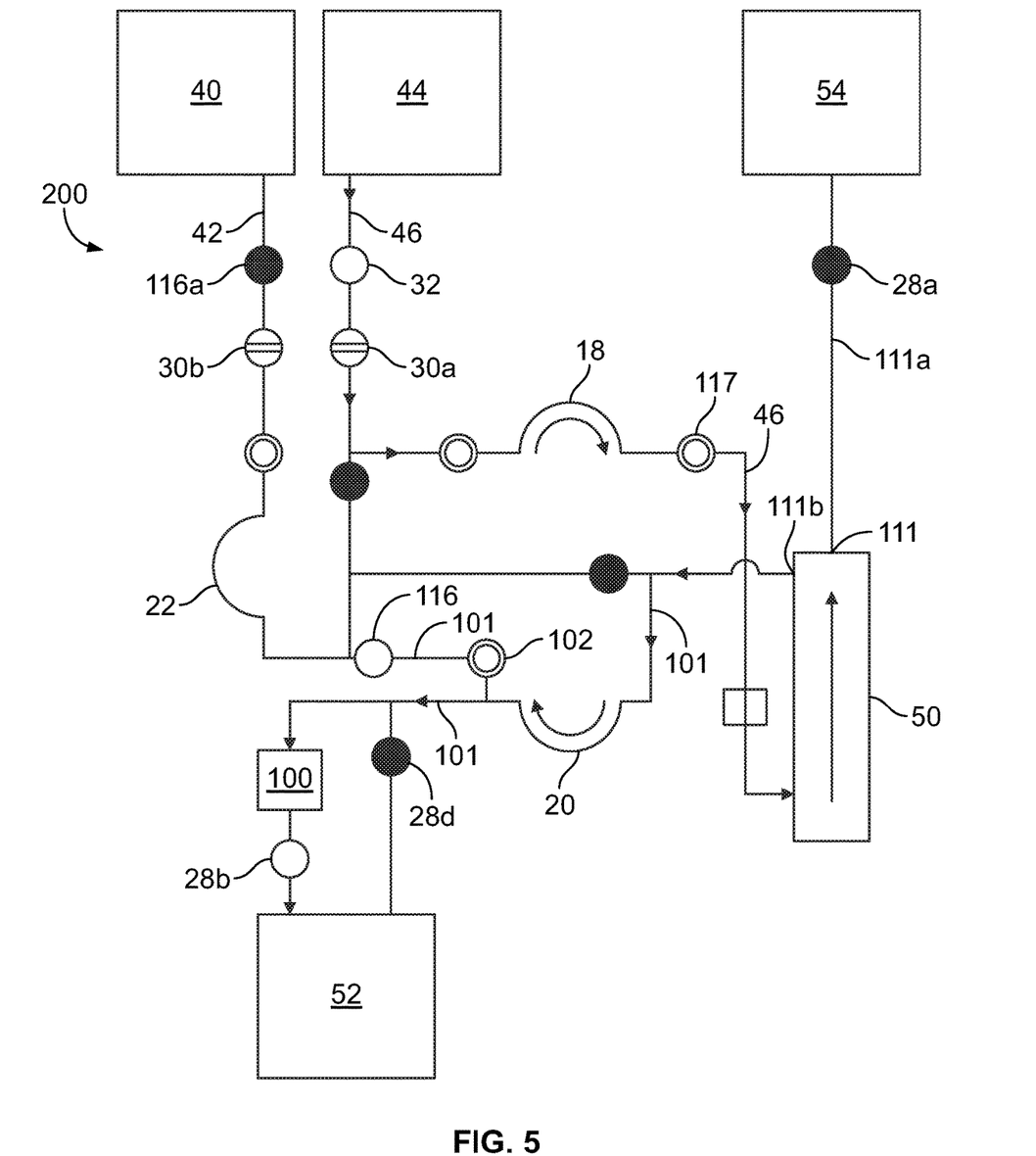
FIG. 5 is a schematic diagram of a blood processing system during an air flush phase of the fluid procedure in which air is used to push remaining retentate without using wash solution, according to an exemplary embodiment.

FIG. 5 is a schematic illustration of the components of the system 200 during an air flush phase of the fluid procedure in which air from the source container 44 may be used to push any remaining retentate in the separator 50 and the leukofilter 100 into container 52 without using wash solution from container 40. During the air flush phase, the source fluid clamp 32 may be opened and air may be withdrawn from container 44. The wash solution clamp 116a may be closed to prevent any fluid remaining in container 40 from entering the fluid circuit 14. The filtrate flow clamp 28a may also be closed so that all air pumped into the separator 50 may exit through retentate outlet 111b. Air from container 44 may be withdrawn via inlet flow path 46 into the separator 50. The flow rate of the air into the separator 50 may be controlled by inlet pump 18, which may pump fluid into the separator 50 at a flow rate determined by a programmable algorithm based on the pressure sensed by leukofilter pressure sensor 102 that will be described further below. Air and any remaining fluid may be pumped out of the retentate outlet 111b of the separator 50 via the outlet pump 20 pumping liquid and air along outlet flow path 101 through leukofilter 100 into the retentate container 52. The outlet pump 20 may be configured to pump air and liquid out of the separator 50 at a flow rate determined by a programmable algorithm incorporating pressure readings from, e.g., the sensor 102. Similarly to the follow-through and fluid flush phases, the leukofilter pressure sensor 102 in communication only with the outlet flow path 101 of outlet pump 20 in the air flush phase may now detect a pressure corresponding only to the flow rate of outlet pump 20.

Segment D of FIG. 6 corresponds to the air flush phase of the fluid procedure (e.g., as shown in FIG. 5) and depicts the leukofilter pressure peaking briefly to about 100 mmHg when air from the separator is pumped through the leukofilter 100 during the air flush phase and then falling to approximately 0 mmHg at the end of the procedure.

Figure 7:
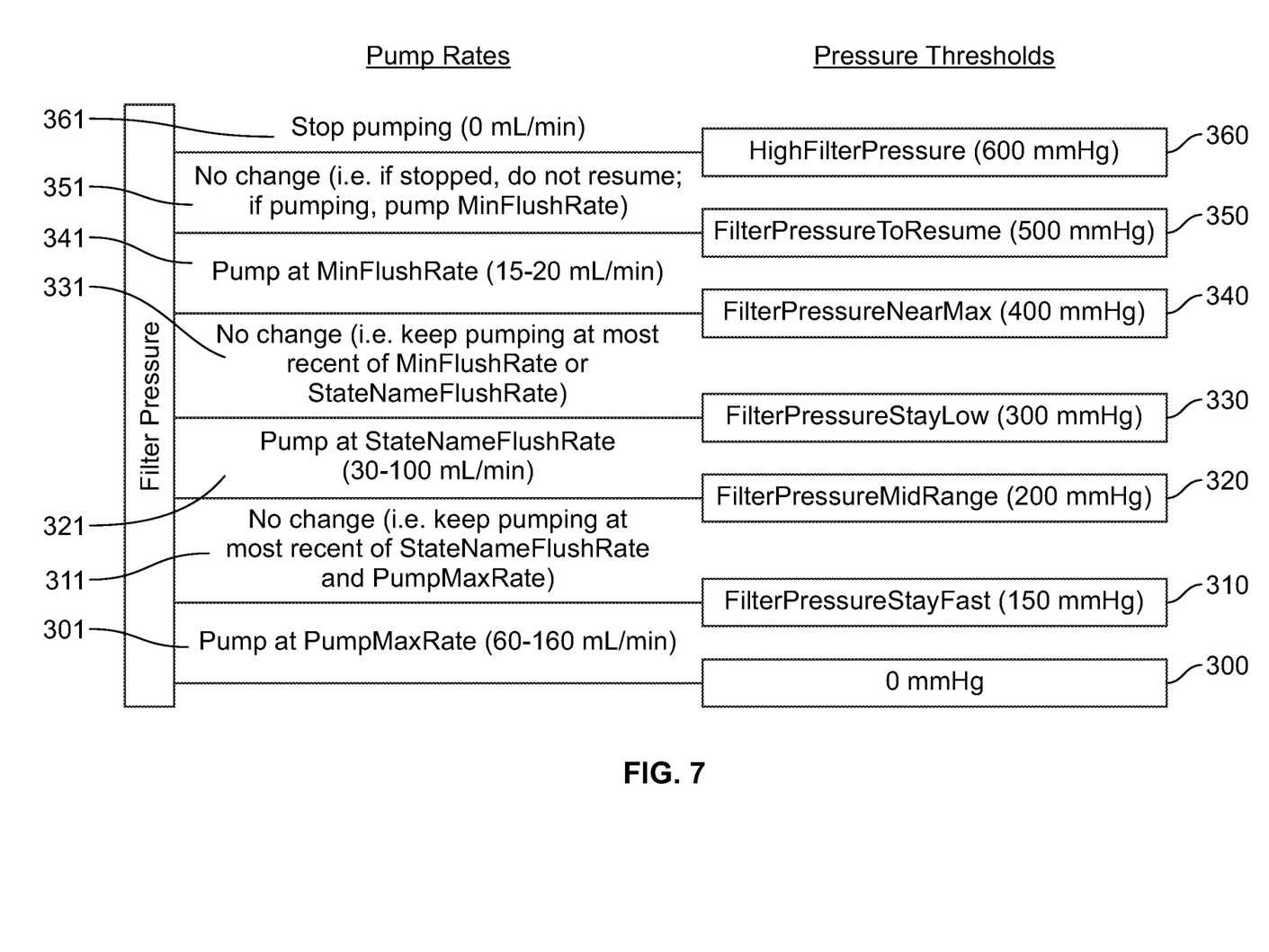
FIG. 7 is a schematic diagram depicting a method of dynamically adjusting fluid flow rate in response to and in order to adjust pressure, according to an exemplary embodiment.

FIG. 7 is a schematic diagram depicting a method by which the controller of the system 200 may dynamically adjust the flow rate of fluid in response to and in order to adjust pressure. Flow rate adjustment will be described with regard to the fluid flush phase (FIG. 4) and air flush phase (FIG. 5), but the method described herein may be applied to other phases of a fluid processing procedure. The programmable controller may be configured to adjust the flow rate at regular or irregular intervals. In one embodiment, the controller may be configured to adjust the flow rate approximately ten times per second based on pressure sensor readings.

In an embodiment in which calculations commence at a state in which there is no fluid flow (no air or liquid flow) in communication with the pressure sensor, e.g., sensor 102 of FIGS. 2-5, the pressure reading may be zero (identified in FIG. 7 at 300), wherein the controller may be configured to pump fluid (identified in FIG. 7 at 301) at a predetermined maximum pump rate (hereinafter "PumpMaxRate") allowable by the system for any phase of the fluid processing procedure. PumpMaxRate may be empirically determined for a fluid processing procedure based on the nature of the fluid being processed and the purpose for processing. For example, when processing whole blood to obtain red blood cells, PumpMaxRate may be set with an objective to minimize procedure time while maintaining an acceptable level of hemolysis. For example, PumpMaxRate may be set to a value of 60-160 mL/min when processing whole blood, depending on, e.g., hemolysis tolerance. The controller may be configured to pump at PumpMaxRate so long as the pressure remains below or equal to a first predetermined threshold (hereinafter "FilterPressureStayFast"). In one embodiment, FilterPressureStayFast may be determined for each phase of the fluid procedure with reference to a nominal pressure value observed/determined for each phase. For example, if the nominal pressure value during the fluid flush phase (FIG. 4) is 250 mmHg, FilterPressureStayFast may be set to a value intermediate to 250 mmHg and zero. In one embodiment, FilterPressureStayFast may be set to 150 mmHg. Therefore, in this embodiment, the controller may be configured to pump at PumpMaxRate so long as the pressure remains in the range of zero to 150 mmHg.

If the pressure is at a value above FilterPressureStayFast (identified in FIG. 7 at 310) but below or equal to a second predetermined threshold (hereinafter "FilterPressureMidRange", which is identified in FIG. 7 at 320), the controller may be configured to pump fluid at the same rate as its most recent pump rate (identified in FIG. 7 at 311). If its most recent pump rate was PumpMaxRate (step 301), the controller may continue to pump at PumpMaxRate. If its most recent pump rate was a lower pump rate (hereinafter "StateNameFlushRate", which is identified in FIG. 7 at 321, and described below), the controller may continue to pump at StateNameFlushRate. The controller may be configured to pump at its most recent pump rate so long as the pressure remains below or equal to FilterPressureMidRange and above FilterPressureStayFast (as in FIG. 7 at 311). In one embodiment, FilterPressureMidRange may be determined with reference to the nominal pressure value and FilterPressureStayFast observed/determined for each phase. For example, if the nominal pressure value during the fluid flush phase (FIG. 4) is 250 mmHg and FilterPressureStayFast is set to 150 mmHg, FilterPressureMidRange may be set to a value intermediate to 250 mmHg and 150 mmHg. In one embodiment, FilterPressureMidRange may be set to 200 mmHg. Therefore, in this embodiment, the controller may be configured to pump at its most recent pump rate so long as the pressure remains above 150 mmHg and equal to or below 200 mmHg.

If the pressure is at a value above FilterPressureMidRange but below or equal to a third predetermined threshold (hereinafter "FilterPressureStaySlow", which is identified in FIG. 7 at 330), the controller may be configured to pump fluid at a predetermined nominal pump rate (the aforementioned StateNameFlushRate, which is identified in FIG. 7 at 321) set for a particular phase of the fluid procedure. StateNameFlushRate may be empirically determined for each phase of the fluid procedure with reference to the nominal pressure value and its corresponding nominal pump rate for the phase. For example, if the nominal pressure value during the fluid flush phase (FIG. 4) is 250 mmHg, its nominal flow rate may be a value in the range of 30-100 mL/min. The controller may be configured to pump at StateNameFlushRate so long as the pressure remains below or equal to FilterPressureStaySlow and above FilterPressureMidRange (as in FIG. 7 at 321). In one embodiment, FilterPressureStaySlow may be determined with reference to the nominal pressure value observed/determined for each phase. For example, if the nominal pressure value during the fluid flush phase (FIG. 4) is 250 mmHg, FilterPressureStaySlow may be set to a value above 250 mmHg. In one embodiment, FilterPressureStaySlow may be set to 300 mmHg. Therefore, in this embodiment, the controller may be configured to pump at StateNameFlushRate so long as the pressure remains above 200 mmHg and equal to or below 300 mmHg.

If the pressure is at a value above FilterPressureStaySlow but below or equal to a fourth predetermined threshold (hereinafter "FilterPressureNearMax", which is identified in FIG. 7 at 340), the controller may be configured to pump fluid at the same rate as its most recent pump rate (identified in FIG. 7 at 331). If its most recent pump rate was StateNameFlushRate, the controller may continue to pump at StateNameFlushRate. If its most recent pump rate was a lower pump rate (hereinafter "MinFlushRate", which is identified in FIG. 7 at 341, and described below), the controller may continue to pump at MinFlushRate. The controller may be configured to pump at its most recent pump rate so long as the pressure remains below or equal to FilterPressureNearMax and above FilterPressureStaySlow (as in FIG. 7 at 331). In one embodiment, FilterPressureNearMax may be determined with reference to a predetermined maximum allowed pressure value (hereinafter "HighFilterPressure", which is identified in FIG. 7 at 360, and described below) and FilterPressureStaySlow for each phase. HighFilterPressure may be empirically determined based on the nature of the fluid being processed and the purpose for processing. For example, when processing whole blood to obtain red blood cells, HighFilterPressure may be set with an objective to minimize hemolysis of cells. For example, HighFilterPressure may be set to a value of 600 mmHg when processing whole blood, depending on, e.g., hemolysis tolerance. If HighFilterPressure is 600 mmHg and FilterPressureStaySlow is set to 300 mmHg, FilterPressureNearMax may be set to a value intermediate to 600 mmHg and 300 mmHg. In one embodiment, FilterPressureNearMax may be set to 400 mmHg. Therefore, in this embodiment, the controller may be configured to pump at its most recent pump rate so long as the pressure remains above 300 mmHg and equal to or below 400 mmHg.

If the pressure is at a value above FilterPressureNearMax but below or equal to a fifth predetermined threshold (hereinafter "FilterPressureToResume", which is identified in FIG. 7 at 350), the controller may be configured to pump fluid at the MinFlushRate (as in FIG. 7 at 341). MinFlushRate may be designated as the pump flow rate at the end of the immediately preceding phase of the fluid procedure from the current phase. For example, if the current phase for which the controller is calculating pump flow rate is the fluid flush phase (FIG. 4), MinFlushRate may be set to the pump rate at the end of the immediately preceding phase, i.e., the follow-through phase (FIG. 3) described above, which pump rate may be 15-20 mL/min in one embodiment. In another example, MinFlushRate may be determined with reference to a nominal pressure value observed/determined for current phase. The controller may be configured to pump at MinFlushRate so long as the pressure remains below or equal to FilterPressureToResume and above FilterPressureNearMax (as in FIG. 7 at 341). In one embodiment, FilterPressureToResume may be determined with reference to HighFilterPressure and/or any of the preceding predetermined thresholds. For example, if HighFilterPressure of 600 mmHg is used, FilterPressureToResume may be set to a value below 600 and above 400 mmHg. In one embodiment, FilterPressureToResume may be set to 500 mmHg. Therefore, in this embodiment, the controller may be configured to pump at MinFlushRate so long as the pressure remains above 400 mmHg and equal to or below 500 mmHg.

If the pressure is at a value above FilterPressureToResume but below or equal to HighFilterPressure, the controller may be configured to pump fluid at the same rate as its most recent pump rate (as identified at 351 in FIG. 7). If its most recent pump rate was MinFlushRate, the controller may continue to pump at MinFlushRate. If its most recent pump rate was a stopped pump (as identified at 361 in FIG. 7, and described below), the controller may stop the pump(s). The controller may be configured to pump at its most recent pump rate so long as the pressure remains below or equal to HighFilterPressure and above FilterPressureToResume (as in FIG. 7 at 351). In an embodiment in which HighFilterPressure is set to 600 mmHg and FilterPressureToResume is set to 500 mmHg, the controller may be configured to pump at its most recent pump rate so long as the pressure remains above 500 mmHg and equal to or below 600 mmHg.

If the pressure is above High FilterPressure, the controller may be configured to stop the pump(s) from pumping (as in FIG. 7 at 361). The system may be configured to provide a response action if the pump has been stopped for a threshold time period, e.g., >2 minutes, due to either having exceeded HighFilterPressure (as in FIG. 7 at 361) or having remained above FilterPressureToResume for the threshold time period after a pump stop event. A response action may comprise the controller terminating the procedure, notifying the operator of high pressure, and/or suspending the procedure pending correction by the operator.

Aspects

Aspect 1. A system for monitoring and controlling fluid pressure during a biological fluid procedure comprising a plurality of procedure phases, the system comprising: a reusable separation apparatus controlled by a controller, wherein the reusable separation apparatus comprises a pressure sensor and a pump having an adjustable flow rate in communication with the controller; and a sterile circuit configured to associate with the reusable separation apparatus and provide a fluid flow path in association with the pressure sensor, wherein the pump is configured to pump fluid through the fluid flow path and the controller is configured to control the pump to: pump fluid through the fluid flow path at a first pre-determined pump rate when the pressure sensor detects a first measured pressure value in the range of zero to a first pre-determined pressure threshold, pump fluid through the fluid flow path at the first pre-determined pump rate when the pressure sensor detects a second measured pressure value greater than the first pre-determined pressure threshold but less than or equal to a second pre-determined pressure threshold and when an immediately preceding pump rate is equal to the first pre-determined pump rate, pump fluid through the fluid flow path at a second pre-determined pump rate when the pressure sensor detects a third measured pressure value greater than the first pre-determined pressure threshold but less than or equal to the second pre-determined pressure threshold and when an immediately preceding pump rate to the second pre-determined pump rate is equal to the second pre-determined pump rate, and pump fluid through the fluid flow path at the second pre-determined pump rate when the pressure sensor detects a fourth measured pressure value greater than the second pre-determined pressure threshold but less than or equal to a third pre-determined pressure threshold.

Aspect 2. The system of Aspect 1, wherein the controller is further configured to control the pump to: pump fluid through the fluid flow path at the second pre-determined pump rate when the pressure sensor detects a fifth measured pressure value greater than the third pre-determined pressure threshold but less than or equal to a fourth pre-determined pressure threshold and when an immediately preceding pump rate is equal to the second pre-determined pump rate, pump fluid through the fluid flow path at a third pre-determined pump rate based on a pump rate from a previous phase or a pump rate associated with a nominal pressure from a current phase when the pressure sensor detects a sixth measured pressure value greater than the third pre-determined pressure threshold but less than or equal to the fourth pre-determined pressure threshold and when an immediately preceding pump rate is equal to the third pre-determined pump rate, and pump fluid through the fluid flow path at the third pre-determined pump rate when the pressure sensor detects a seventh measured pressure value greater than the fourth pre-determined pressure threshold but less than or equal to a fifth pre-determined pressure threshold.

Aspect 3. The system of Aspect 2, wherein the controller is further configured to control the pump to: pump fluid through the fluid flow path at the third pre-determined pump rate when the pressure sensor detects an eighth measured pressure value greater than the fifth pre-determined pressure threshold but less than or equal to a sixth pre-determined pressure threshold and when an immediately preceding pump rate is equal to the third pre-determined pump rate, pump fluid through the fluid flow path at a fourth pre-determined pump rate when the pressure sensor detects a ninth measured pressure value greater than the fifth pre-determined pressure threshold but less than or equal to the sixth pre-determined pressure threshold and when an immediately preceding pump rate is equal to the fourth pre-determined pump rate, and pump fluid through the fluid flow path at the fourth pre-determined pump rate when the pressure sensor detects a tenth measured pressure value greater than the sixth pre-determined pressure threshold.

Aspect 4. The system of Aspect 3, wherein the fourth pre-determined pump rate is less than the third pre-determined pump rate, which is less than the second pre-determined pump rate, which is less than the first pre-determined pump rate.

Aspect 5. The system of Aspect 3, wherein the first pre-determined pump rate is in the range of 60-160 mL/min, the second pre-determined pump rate is in the range of 30-100 mL/min, and the fourth pre-determined pump rate is zero.

Aspect 6. The system of Aspect 3, wherein the sixth pre-determined pressure threshold is less than or equal to 600 mmHg.

Aspect 7. The system of Aspect 3, wherein the controller is configured to provide a response action when the pump has been operating at the fourth pre-determined pump rate for a threshold time period, and the response action comprises at least one of terminating the biological fluid procedure, notifying an operator of high pressure, and suspending the biological fluid procedure pending correction by the operator.

Aspect 8. The system of Aspect 1, wherein the pressure sensor is configured to be in communication with an inlet of a leukofilter and to communicate to the controller pressure at the inlet of the leukofilter.

Aspect 9. The system of Aspect 1, wherein the pump comprises a plurality of pumps configured to contribute collectively to pressure detected by the pressure sensor.

Aspect 10. The system of Aspect 1, wherein the first and/or second pre-determined pressure thresholds are determined empirically for each procedure phase of the plurality of procedure phases.

Aspect 11. A method for monitoring and controlling fluid pressure during a biological fluid procedure comprising a plurality of procedure phases, the method comprising: conveying fluid through a fluid flow path at a first pre-determined rate when a first measured pressure value in the range of zero to a first pre-determined pressure threshold is detected; conveying fluid through the fluid flow path at the first pre-determined rate when a second measured pressure value greater than the first pre-determined pressure threshold but less than or equal to a second pre-determined pressure threshold is detected and when an immediately preceding rate is equal to the first pre-determined rate; conveying fluid through the fluid flow path at a second pre-determined rate when a third measured pressure value greater than the first pre-determined pressure threshold but less than or equal to the second pre-determined pressure threshold is detected and when an immediately preceding rate is equal to the second pre-determined rate; and conveying fluid through the fluid flow path at the second pre-determined rate when a fourth measured pressure value greater than the second pre-determined pressure threshold but less than or equal to a third pre-determined pressure threshold is detected.

Aspect 12. The method of Aspect 11, further comprising: conveying fluid through the fluid flow path at the second pre-determined rate when a fifth measured pressure value greater than the third pre-determined pressure threshold but less than or equal to a fourth pre-determined pressure threshold is detected and when an immediately preceding rate is equal to the second pre-determined rate, conveying fluid through the fluid flow path at a third pre-determined rate comprising a rate from a previous phase when a sixth measured pressure value greater than the third pre-determined pressure threshold but less than or equal to the fourth pre-determined pressure threshold is detected and when an immediately preceding rate is equal to the third pre-determined rate, and conveying fluid through the fluid flow path at the third pre-determined rate when a seventh measured pressure value greater than the fourth pre-determined pressure threshold but less than or equal to a fifth pre-determined pressure threshold is detected.

Aspect 13. The method of Aspect 12, further comprising: conveying fluid through the fluid flow path at the third pre-determined rate when an eighth measured pressure value greater than the fifth pre-determined pressure threshold but less than or equal to a sixth pre-determined pressure threshold is detected and when an immediately preceding rate is equal to the third pre-determined rate, conveying fluid through the fluid flow path at a fourth pre-determined rate when a ninth measured pressure value greater than the fifth pre-determined pressure threshold but less than or equal to the sixth pre-determined pressure threshold is detected and when an immediately preceding rate is equal to the fourth pre-determined rate, and conveying fluid through the fluid flow path at the fourth pre-determined rate when a tenth measured pressure value greater than the sixth pre-determined pressure threshold is detected.

Aspect 14. The method of Aspect 13, wherein the fourth pre-determined rate is less than the third pre-determined rate, which is less than the second pre-determined rate, which is less than the first pre-determined rate.

Aspect 15. The method of Aspect 13, wherein the first pre-determined rate is in the range of 60-160 mL/min, the second pre-determined rate is in the range of 30-100 mL/min, and the fourth pre-determined rate is zero.

Aspect 16. The method of Aspect 13, further comprising providing a response action when fluid has been conveyed through the fluid flow path at the fourth pre-determined rate for a threshold time period, wherein the response action comprises at least one of terminating the biological fluid procedure, notifying an operator of high pressure, and suspending the biological fluid procedure pending correction by the operator.

Aspect 17. The method of Aspect 11, wherein pressure is detected at an inlet of a leukofilter.

Aspect 18. The method of Aspect 11, wherein fluid is conveyed through the fluid flow circuit by a plurality of pumps which contribute collectively to the pressure that is detected.

Aspect 19. The method of Aspect 11, wherein the first and/or second pre-determined pressure thresholds are determined empirically for each procedure phase of the plurality of procedure phases.

Aspect 20. A method for monitoring and controlling fluid pressure during a biological fluid procedure comprising a plurality of procedure phases, the method comprising: conveying fluid through a fluid flow path at a first pre-determined rate when a first measured pressure value in the range of zero to a first pre-determined pressure threshold is detected; conveying fluid through the fluid flow path at the first pre-determined rate when a second measured pressure value greater than the first pre-determined pressure threshold but less than or equal to a second pre-determined pressure threshold is detected and when an immediately preceding rate is equal to the first pre-determined rate; conveying fluid through the fluid flow path at a second pre-determined rate when a third measured pressure value greater than the first pre-determined pressure threshold but less than or equal to the second pre-determined pressure threshold is detected and when an immediately preceding rate is equal to the second pre-determined rate; conveying fluid through the fluid flow path at the second pre-determined rate when a fourth measured pressure value greater than the second pre-determined pressure threshold but less than or equal to a third pre-determined pressure threshold is detected; conveying fluid through the fluid flow path at the second pre-determined rate when a fifth measured pressure value greater than the third pre-determined pressure threshold but less than or equal to a fourth pre-determined pressure threshold is detected and when an immediately preceding rate is equal to the second pre-determined rate; conveying fluid through the fluid flow path at a third pre-determined rate comprising a rate from a previous phase when a sixth measured pressure value greater than the third pre-determined pressure threshold but less than or equal to the fourth pre-determined pressure threshold is detected and when an immediately preceding rate is equal to the third pre-determined rate; conveying fluid through the fluid flow path at the third pre-determined rate when a seventh measured pressure value greater than the fourth pre-determined pressure threshold but less than or equal to a fifth pre-determined pressure threshold is detected; conveying fluid through the fluid flow path at the third pre-determined rate when an eighth measured pressure value greater than the fifth pre-determined pressure threshold but less than or equal to a sixth pre-determined pressure threshold is detected and when an immediately preceding rate is equal to the third pre-determined rate; conveying fluid through the fluid flow path at a fourth pre-determined rate when a ninth measured pressure value greater than the fifth pre-determined pressure threshold but less than or equal to the sixth pre-determined pressure threshold is detected and when an immediately preceding rate is equal to the fourth pre-determined rate; and conveying fluid through the fluid flow path at the fourth pre-determined rate when a tenth measured pressure value greater than the sixth pre-determined pressure threshold is detected.

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

The invention claimed is:

1. A system for monitoring and controlling fluid pressure during a biological fluid separation procedure comprising a plurality of phases in which a separated fluid constituent is pumped through a leukofilter, the system comprising:
   a reusable separation apparatus controlled by a programmable controller, wherein the reusable separation apparatus comprises a biological fluid separator, a leukofilter pressure sensor, and a pump having an adjustable pump rate in communication with the controller; and
   a sterile circuit configured to associate with the reusable separation apparatus and provide a fluid flow path including a leukofilter in association with the leukofilter pressure sensor, wherein the controller is programmed to control the biological fluid separator to separate a fluid constituent from a biological fluid, the pump is configured to pump the separated fluid constituent through the leukofilte, and the controller is configured further programmed to control the pump to:
      pump the separated fluid constituent through the leukofilter at a first pre-determined pump rate when the leukofilter pressure sensor detects a first measured pressure value in the range of zero to a first pre-determined pressure threshold,
      pump the separated fluid constituent through the leukofilter at the first pre-determined pump rate when the leukofilter pressure sensor detects a second measured pressure value greater than the first pre-determined pressure threshold but less than or equal to a second pre-determined pressure threshold and when an immediately preceding pump rate is equal to the first pre-determined pump rate,
      pump the separated fluid constituent through the leukofilter at a second pre-determined pump rate when the leukofilter pressure sensor detects a third measured pressure value greater than the first pre-determined pressure threshold but less than or equal to the second pre-determined pressure threshold and when an immediately preceding pump rate is equal to the second pre-determined pump rate, and
      pump the separated fluid constituent through the leukofilter at the second pre-determined pump rate when the leukofilter pressure sensor detects a fourth measured pressure value greater than the second pre-determined pressure threshold but less than or equal to a third pre-determined pressure threshold, and wherein the controller is further programmed to employ different pre-determined pressure thresholds for at least two of the phases in which the separated fluid constituent is pumped through the leukofilter.

2. The system of claim 1, wherein the controller is further programmed to control the pump to:
   pump the separated fluid constituent through the leukofilter at the second pre-determined pump rate when the leukofilter pressure sensor detects a fifth measured pressure value greater than the third pre-determined pressure threshold but less than or equal to a fourth pre-determined pressure threshold and when an immediately preceding pump rate is equal to the second pre-determined pump rate, pump the separated fluid constituent through the leukofilter at a third pre-determined pump rate based on a pump rate from a previous phase or a pump rate associated with a nominal pressure from a current phase when the leukofilter pressure sensor detects a sixth measured pressure value greater than the third pre-determined pressure threshold but less than or equal to the fourth pre-determined pressure threshold and when an immediately preceding pump rate is equal to the third pre-determined pump rate, and pump the separated fluid constituent through the leukofilter at the third pre-determined pump rate when the leukofilter pressure sensor detects a seventh measured pressure value greater than the fourth pre-determined pressure threshold but less than or equal to a fifth pre-determined pressure threshold.

3. The system of claim 2, wherein the controller is further programmed to control the pump to:

pump the separated fluid constituent through the leukofilter at the third pre-determined pump rate when the leukofilter pressure sensor detects an eighth measured pressure value greater than the fifth pre-determined pressure threshold but less than or equal to a sixth pre-determined pressure threshold and when an immediately preceding pump rate is equal to the third pre-determined pump rate, pump the separated fluid constituent through the leukofilter at a fourth pre-determined pump rate when the leukofilter pressure sensor detects a ninth measured pressure value greater than the fifth pre-determined pressure threshold but less than or equal to the sixth pre-determined pressure threshold and when an immediately preceding pump rate is equal to the fourth pre-determined pump rate, and pump the separated fluid constituent through the leukofilter at the fourth pre-determined pump rate when the leukofilter pressure sensor detects a tenth measured pressure value greater than the sixth pre-determined pressure threshold.

4. The system of claim 3, wherein the fourth pre-determined pump rate is less than the third pre-determined pump rate, which is less than the second pre-determined pump rate, which is less than the first pre-determined pump rate.

5. The system of claim 3, wherein the first pre-determined pump rate is in the range of 60-160 mL/min, the second pre-determined pump rate is in the range of 30-100 mL/min, and the fourth pre-determined pump rate is zero.

6. The system of claim 3, wherein the sixth pre-determined pressure threshold is less than or equal to 600 mmHg.

7. The system of claim 3, wherein
the controller is programmed to provide a response action when the pump has been operating at the fourth pre-determined pump rate for a threshold time period, and
the response action comprises at least one of terminating the biological fluid processing procedure, notifying an operator of high pressure, and suspending the biological fluid processing procedure pending correction by the operator.

8. The system of claim 1, wherein the leukofilter pressure sensor is configured to be in communication with an inlet of the leukofilter and to communicate to the controller pressure at the inlet of the leukofilter.

9. The system of claim 1, wherein the pump comprises a plurality of pumps configured to contribute collectively to pressure detected by the leukofilter pressure sensor.

10. The system of claim 1, wherein the first and/or second pre-determined pressure thresholds are determined empirically for each of the plurality of phases in which the separated fluid constituent is pumped through the leukofilter.

11. A method for monitoring and controlling fluid pressure during a biological fluid separation procedure comprising a plurality of phases in which a separated fluid constituent is pumped through a leukofilter, the method comprising:

separating a fluid constituent from a biological fluid;
pumping the separated fluid constituent through the leukofilter at a first pre-determined rate when a first measured leukofilter pressure value in the range of zero to a first pre-determined pressure threshold is detected;
pumping the separated fluid constituent through the leukofilter at the first pre-determined rate when a second measured leukofilter pressure value greater than the first pre-determined pressure threshold but less than or equal to a second pre-determined pressure threshold is detected and when an immediately preceding rate is equal to the first pre-determined rate;
pumping the separated fluid constituent through the leukofilter at a second pre-determined rate when a third measured leukofilter pressure value greater than the first pre-determined pressure threshold but less than or equal to the second pre-determined pressure threshold is detected and when an immediately preceding rate is equal to the second pre-determined rate; and
pumping the separated fluid constituent through the leukofilter at the second pre-determined rate when a fourth measured leukofilter pressure value greater than the second pre-determined pressure threshold but less than or equal to a third pre-determined pressure threshold is detected, wherein different pre-determined pressure thresholds are employed for at least two of the phases in which the separated fluid constituent is pumped through the leukofilter.

12. The method of claim 11, further comprising:
pumping the separated fluid constituent through the leukofilter at the second pre-determined rate when a fifth measured leukofilter pressure value greater than the third pre-determined pressure threshold but less than or equal to a fourth pre-determined pressure threshold is detected and when an immediately preceding rate is equal to the second pre-determined rate,
pumping the separated fluid constituent through the leukofilter at a third pre-determined rate comprising a rate from a previous phase when a sixth measured leukofilter pressure value greater than the third pre-determined pressure threshold but less than or equal to the fourth pre-determined pressure threshold is detected and when an immediately preceding rate is equal to the third pre-determined rate, and
pumping the separated fluid constituent through the leukofilter at the third pre-determined rate when a seventh measured leukofilter pressure value greater than the fourth pre-determined pressure threshold but less than or equal to a fifth pre-determined pressure threshold is detected.

13. The method of claim 12, further comprising:
pumping the separated fluid constituent through the leukofilter at the third pre-determined rate when an eighth measured leukofilter pressure value greater than the fifth pre-determined pressure threshold but less than or equal to a sixth pre-determined pressure threshold is detected and when an immediately preceding rate is equal to the third pre-determined rate,
pumping the separated fluid constituent through the leukofilter at a fourth pre-determined rate when a ninth measured leukofilter pressure value greater than the fifth pre-determined pressure threshold but less than or equal to the sixth pre-determined pressure threshold is detected and when an immediately preceding rate is equal to the fourth pre-determined rate, and
pumping the separated fluid constituent through the leukofilter at the fourth pre-determined rate when a tenth leukofilter measured pressure value greater than the sixth pre-determined pressure threshold is detected.

14. The method of claim 13, wherein the fourth pre-determined rate is less than the third pre-determined rate, which is less than the second pre-determined rate, which is less than the first pre-determined rate.

15. The method of claim 13, wherein the first pre-determined rate is in the range of 60-160 mL/min, the second pre-determined rate is in the range of 30-100 mL/min, and the fourth pre-determined rate is zero.

16. The method of claim 13, further comprising providing a response action when fluid has been conveyed through the leukofilter at the fourth pre-determined rate for a threshold time period, wherein the response action comprises at least one of terminating the biological fluid processing procedure, notifying an operator of high pressure, and suspending the biological fluid processing procedure pending correction by the operator.

17. The method of claim 11, wherein pressure is detected at an inlet of the leukofilter.

18. The method of claim 11, wherein the separated fluid constituent is conveyed through the leukofilter by a plurality of pumps which contribute collectively to the leukofilter pressure that is detected.

19. The method of claim 11, wherein the first and/or second pre-determined pressure thresholds are determined empirically for each of the plurality of phases in which the separated fluid constituent is pumped through the leukofilter.

20. A method for monitoring and controlling fluid pressure during a biological fluid processing separation procedure comprising a plurality of phases in which a separated fluid constituent is pumped through a leukofilter, the method comprising:
separating a fluid constituent from a biological fluid;
pumping the separated fluid constituent through a leukofilter at a first pre-determined rate when a first measured leukofilter pressure value in the range of zero to a first pre-determined pressure threshold is detected;
pumping the separated fluid constituent through the leukofilter at the first pre-determined rate when a second measured leukofilter pressure value greater than the first pre-determined pressure threshold but less than or equal to a second pre-determined pressure threshold is detected and when an immediately preceding rate is equal to the first pre-determined rate;
pumping the separated fluid constituent through the leukofilter at a second pre-determined rate when a third measured leukofilter pressure value greater than the first pre-determined pressure threshold but less than or equal to the second pre-determined pressure threshold is detected and when an immediately preceding rate is equal to the second pre-determined rate;
pumping the separated fluid constituent through the leukofilter at the second pre-determined rate when a fourth leukofilter measured pressure value greater than the second pre-determined pressure threshold but less than or equal to a third pre-determined pressure threshold is detected;
pumping the separated fluid constituent through the leukofilter at the second pre-determined rate when a fifth measured leukofilter pressure value greater than the third pre-determined pressure threshold but less than or equal to a fourth pre-determined pressure threshold is detected and when an immediately preceding rate is equal to the second pre-determined rate;
pumping the separated fluid constituent through the leukofilter at a third pre-determined rate comprising a rate from a previous phase when a sixth measured leukofilter pressure value greater than the third pre-determined pressure threshold but less than or equal to the fourth pre-determined pressure threshold is detected and when an immediately preceding rate is equal to the third pre-determined rate;
pumping the separated fluid constituent through the leukofilter at the third pre-determined rate when a seventh measured leukofilter pressure value greater than the fourth pre-determined pressure threshold but less than or equal to a fifth pre-determined pressure threshold is detected;
pumping the separated fluid constituent through the leukofilter at the third pre-determined rate when an eighth measured leukofilter pressure value greater than the fifth pre-determined pressure threshold but less than or equal to a sixth pre-determined pressure threshold is detected and when an immediately preceding rate is equal to the third pre-determined rate;
pumping the separated fluid constituent through the leukofilter at a fourth pre-determined rate when a ninth measured leukofilter pressure value greater than the fifth pre-determined pressure threshold but less than or equal to the sixth pre-determined pressure threshold is detected and when an immediately preceding rate is equal to the fourth pre-determined rate; and
pumping the separated fluid constituent through the leukofilter at the fourth pre-determined rate when a tenth measured leukofilter pressure value greater than the sixth pre-determined pressure threshold is detected, wherein different pre-determined thresholds are employed for at least two of the phases in which the separated fluid constituent is pumped through the leukofilter.

* * * * *